(12) United States Patent
Sansoucy

(10) Patent No.: US 8,394,218 B2
(45) Date of Patent: Mar. 12, 2013

(54) METHOD FOR MAKING A MULTI-LUMEN CATHETER HAVING A SEPARATED TIP SECTION

(75) Inventor: Michael R. Sansoucy, Wrentham, MA (US)

(73) Assignee: Covidien LP, Mansfield, MA (US)

( * ) Notice: Subject to any disclaimer, the term of this patent is extended or adjusted under 35 U.S.C. 154(b) by 363 days.

(21) Appl. No.: 12/835,170

(22) Filed: Jul. 13, 2010

(65) Prior Publication Data

US 2011/0011525 A1 Jan. 20, 2011

Related U.S. Application Data

(60) Provisional application No. 61/226,881, filed on Jul. 20, 2009.

(51) Int. Cl.
*B29C 65/68* (2006.01)
*B29C 65/02* (2006.01)
*A61M 25/14* (2006.01)

(52) U.S. Cl. ............ 156/85; 156/304.2; 156/304.6; 604/6.16; 604/284; 29/447

(58) Field of Classification Search ............ 156/304.2, 156/304.5, 304.6, 85, 86; 604/6.16, 284; 29/447, DIG. 35; 285/381.4
See application file for complete search history.

(56) References Cited

U.S. PATENT DOCUMENTS

| | | |
|---|---|---|
| 4,309,994 A | 1/1982 | Grunwald |
| 4,636,272 A * | 1/1987 | Riggs ............................ 156/158 |
| 4,925,452 A | 5/1990 | Melinyshyn et al. |
| 5,197,976 A | 3/1993 | Herweck et al. |
| 5,254,084 A | 10/1993 | Geary |
| 5,273,534 A | 12/1993 | Knoepfler |
| 5,476,453 A | 12/1995 | Mehta |
| 5,599,304 A | 2/1997 | Shaari |
| 5,624,413 A | 4/1997 | Markel et al. |
| 5,695,457 A | 12/1997 | St. Goar et al. |
| 5,704,915 A | 1/1998 | Melsky et al. |
| 5,718,692 A | 2/1998 | Schon et al. |
| 5,776,111 A | 7/1998 | Tesio |
| 5,800,414 A | 9/1998 | Cazal |
| 5,807,311 A | 9/1998 | Palestrant |
| 5,947,953 A | 9/1999 | Ash et al. |
| 5,957,912 A | 9/1999 | Heitzmann |
| 5,964,796 A | 10/1999 | Imran |
| 6,001,079 A | 12/1999 | Pourchez |
| 6,074,374 A | 6/2000 | Fulton |
| 6,117,117 A | 9/2000 | Mauch |
| 6,156,016 A | 12/2000 | Maginot |

(Continued)

FOREIGN PATENT DOCUMENTS

WO WO 01/32240 A1 5/2001
WO WO 2009/051967 A1 4/2009

(Continued)

OTHER PUBLICATIONS

European Search Report from European Application No. EP 10 16 9954 dated Oct. 27, 2010.

*Primary Examiner* — Michael Tolin
(74) *Attorney, Agent, or Firm* — John Paul Mello, Esq.

(57) ABSTRACT

The present disclosure is directed to a method of manufacturing a catheter wherein a dual lumen catheter body and at least one distal tip member are separately formed and the at least one distal tip member is subsequently assembled to the dual lumen catheter body. The components may be assembled using a heating process or, alternatively, using adhesives.

17 Claims, 3 Drawing Sheets

U.S. PATENT DOCUMENTS

| | | |
|---|---|---|
| 6,190,349 B1 | 2/2001 | Ash et al. |
| 6,475,207 B1 | 11/2002 | Maginot et al. |
| 6,482,169 B1 | 11/2002 | Kuhle |
| 6,513,527 B1 | 2/2003 | Abdel-Aziz |
| 6,558,356 B2 | 5/2003 | Barbut |
| 6,585,705 B1 | 7/2003 | Maginot et al. |
| 6,638,242 B2 | 10/2003 | Wilson et al. |
| 6,682,519 B1 | 1/2004 | Schon |
| 6,695,832 B2 | 2/2004 | Schon et al. |
| 6,719,749 B1 | 4/2004 | Schweikert et al. |
| 6,723,084 B1 | 4/2004 | Maginot et al. |
| 6,743,218 B2 | 6/2004 | Maginot et al. |
| 6,758,836 B2 | 7/2004 | Zawacki |
| 6,872,198 B1 | 3/2005 | Wilson et al. |
| 6,881,211 B2 | 4/2005 | Schweikert et al. |
| 6,913,601 B2 | 7/2005 | St. Goar et al. |
| 6,916,313 B2 | 7/2005 | Cunningham |
| 6,921,396 B1 | 7/2005 | Wilson et al. |
| 6,966,886 B2 | 11/2005 | Appling |
| 6,997,894 B2 | 2/2006 | Caresio |
| 7,008,412 B2 | 3/2006 | Maginot |
| 7,013,928 B2 | 3/2006 | Navis |
| 7,018,374 B2 | 3/2006 | Schon et al. |
| RE39,451 E | 12/2006 | Kuhle |
| D550,839 S | 9/2007 | Zawacki et al. |
| 7,300,430 B2 | 11/2007 | Wilson et al. |
| 7,347,852 B2 | 3/2008 | Hobbs et al. |
| 7,381,204 B2 | 6/2008 | Wilson et al. |
| 7,393,339 B2 | 7/2008 | Zawacki et al. |
| 2002/0099326 A1 | 7/2002 | Wilson et al. |
| 2002/0133112 A1 | 9/2002 | Navis |
| 2003/0032918 A1 | 2/2003 | Quinn |
| 2003/0088213 A1 | 5/2003 | Schweikert et al. |
| 2004/0059314 A1 | 3/2004 | Schon et al. |
| 2004/0092863 A1 | 5/2004 | Raulerson et al. |
| 2004/0171997 A1 | 9/2004 | Wilson et al. |
| 2004/0172003 A1 | 9/2004 | Wilson et al. |
| 2004/0210187 A1 | 10/2004 | Zawacki |
| 2004/0243095 A1 | 12/2004 | Nimkar et al. |
| 2005/0054990 A1 | 3/2005 | Graft et al. |
| 2005/0059925 A1 | 3/2005 | Maginot et al. |
| 2005/0096585 A1 | 5/2005 | Schon et al. |
| 2005/0171469 A1 | 8/2005 | Cunningham |
| 2005/0187535 A1 | 8/2005 | Wilson et al. |
| 2005/0197624 A1 | 9/2005 | Goodson, IV et al. |
| 2005/0277862 A1 | 12/2005 | Anand |
| 2005/0283111 A1 | 12/2005 | Maurice |
| 2007/0005003 A1 * | 1/2007 | Patterson et al. ............... 604/43 |
| 2007/0060866 A1 | 3/2007 | Raulerson et al. |
| 2007/0078438 A1 | 4/2007 | Okada |
| 2007/0106206 A1 | 5/2007 | Appling |
| 2007/0233042 A1 | 10/2007 | Moehle et al. |
| 2008/0009803 A1 | 1/2008 | Schon et al. |
| 2008/0009832 A1 | 1/2008 | Barron et al. |
| 2008/0021417 A1 | 1/2008 | Zawacki et al. |
| 2008/0033350 A1 | 2/2008 | Wilson et al. |
| 2008/0039774 A1 | 2/2008 | Zawacki et al. |
| 2008/0045886 A1 | 2/2008 | Hobbs et al. |
| 2008/0214980 A1 | 9/2008 | Anand |
| 2009/0204052 A1 * | 8/2009 | Nimkar et al. ............... 604/6.16 |

FOREIGN PATENT DOCUMENTS

WO  WO 2009/051969 A1  4/2009

* cited by examiner

METHOD FOR MAKING A MULTI-LUMEN CATHETER HAVING A SEPARATED TIP SECTION

The present application claims the benefit of and priority to U.S. Provisional Patent Application No. 61/226,881, filed on Jul. 20, 2009, which is incorporated herein by reference in its entirety.

BACKGROUND

1. Technical Field

The present disclosure relates to a method for manufacturing a multi-lumen catheter and, more particularly, to a method for manufacturing a multi-lumen catheter having a separated tip section.

2. Background of Related Art

Catheters for supplying and/or withdrawing fluids into and/or from the body are well known in the art and may be employed for medication delivery, urine removal and blood treatment, e.g., hemodialysis, to name a few. Single and multilumen catheters are well known. Typically, catheters used for hemodialysis are multilumen catheters and include a body which defines an arterial lumen and a venous lumen. During an exemplary hemodialysis procedure, a distal portion of a multilumen catheter is inserted into a patient and blood is withdrawn through the arterial lumen of the catheter. The withdrawn blood is supplied to a hemodialysis unit which purifies the blood by removing waste and toxins from the blood. Thereafter, the purified blood is returned to the patient through the venous lumen of the catheter.

One problem associated with multilumen dialysis catheters is the potential for recirculation of blood from the distal end of the venous lumen through the distal end of the arterial lumen. In an effort to minimize blood recirculation, catheters have been developed in which the arterial lumen and the venous lumen openings are laterally spaced. These catheters minimize blood recirculation by distancing the arterial lumen distal opening from the venous lumen distal opening.

Catheters can be manufactured using a variety of different techniques including, for example, thermoforming, extrusion, blow molding, rotational molding and injection molding. However, the manufacturing of dual lumen catheters with laterally spaced or separated tip sections complicates known catheter manufacturing processes.

Accordingly, a continuing need exists in the medical arts for a simpler, cost effective method for manufacturing a catheter a separated tip section.

SUMMARY

This disclosure relates to a method of manufacturing a multilumen catheter having a separate tip section. In one embodiment, the method comprises the following steps:
   i) forming a dual lumen catheter body having a proximal end and a distal end and defining a first lumen and a second lumen, the dual lumen catheter body defining a first longitudinal axis;
   ii) forming a first distal tip member defining a first distal lumen portion; and
   iii) assembling the first distal tip member to the distal end of the catheter portion such that the first distal lumen portion is in fluid communication with the first lumen.

In one embodiment, the assembling step includes using adhesives to secure the first distal tip member to the distal end of the dual lumen catheter body. Alternatively, the assembling step includes using heat to secure the first distal tip member to the distal end of the dual lumen catheter body.

In one embodiment, the first distal tip member defines a second longitudinal axis and the assembling step includes positioning the second longitudinal axis of the distal tip member at an angle β in relation to the first longitudinal axis of the dual lumen catheter body. Angle β is greater than 0 degrees and may be about 5 degrees or greater. Alternatively, angle β may be about 10 degrees or greater.

In another embodiment, the method further includes the following steps:
   iv) forming a second distal tip member defining a second distal lumen portion; and
   v) assembling the second distal tip member to the distal end of the catheter portion such that the second distal lumen portion is in fluid communication with the second lumen of the dual lumen catheter body.

As discussed above, the assembling steps may include using adhesives or heat to secure the first and second distal tip members to the distal end of the dual lumen catheter body.

In one embodiment, the first distal tip member defines a second longitudinal axis and the second distal tip member defines a third longitudinal axis, and the assembling steps include securing the first and second distal tip members to the dual lumen catheter body such that the second longitudinal axis is disposed at an angle β to the third longitudinal axis. The angle β may be about 5 degrees or greater. Alternatively, the angle β may be about 10 degrees or greater.

In another embodiment, the second longitudinal axis is substantially parallel to the first longitudinal axis. Alternatively, the second and the third longitudinal axes are both disposed at an angle in relation to the first longitudinal axis.

BRIEF DESCRIPTION OF THE DRAWINGS

Various embodiments of the presently disclosed method for manufacturing a multilumen catheter having a separated tip configuration are disclosed herein with reference to the drawings, wherein.

DETAILED DESCRIPTION OF EMBODIMENTS

Figure 1:
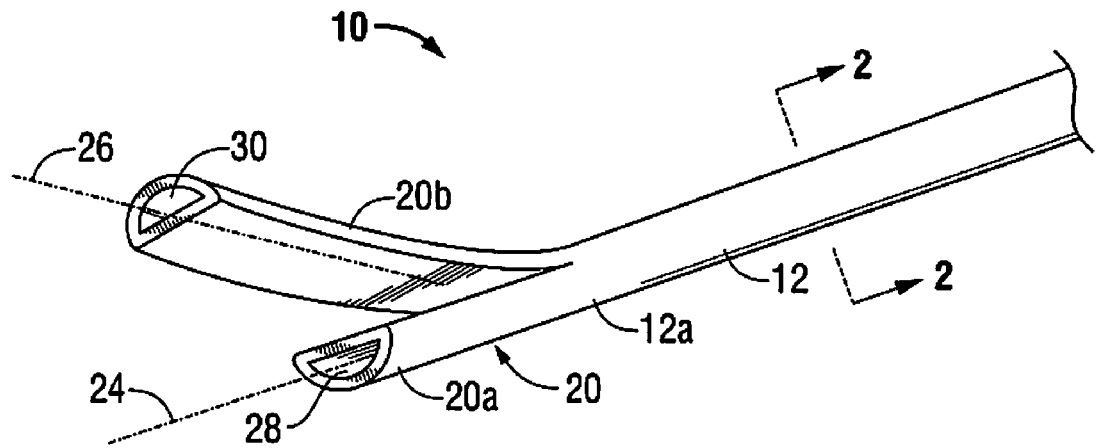
FIG. 1 is a side, perspective view from the distal end of a multilumen catheter formed using the presently disclosed method of manufacturing.

Embodiments of the presently disclosed method of manufacturing split-tip multilumen catheters will now be described in detail with reference to the drawings wherein like reference numerals designate identical or corresponding elements in each of the several views.

The exemplary embodiments of the catheter disclosed herein are discussed in terms of medical catheters for the administration of fluids (withdrawal or introduction) relative to the body of a subject and, more particularly, in terms of a hemodialysis catheter. However, it is envisioned that the present disclosure may be employed with a range of catheter applications including surgical, diagnostic and related treatments of diseases and body ailments of a subject. It is further envisioned that the principles relating to the catheter disclosed include employment with various catheter related procedures, such as, for example, hemodialysis, cardiac, abdominal, urinary, intestinal, and in chronic and acute applications. Moreover, the catheter can be used for administration of fluids such as, for example, medication, saline, bodily fluids, blood and urine.

In the discussion that follows, the term "proximal" or "trailing" will refer to the portion of a structure that is closer to a clinician, while the term "distal" or "leading" will refer to the portion that is further from the clinician. As used herein, the term "subject" refers to a human patient or other animal. The term "clinician" refers to a doctor, nurse or other care provider and may include support personnel.

Figure 2:
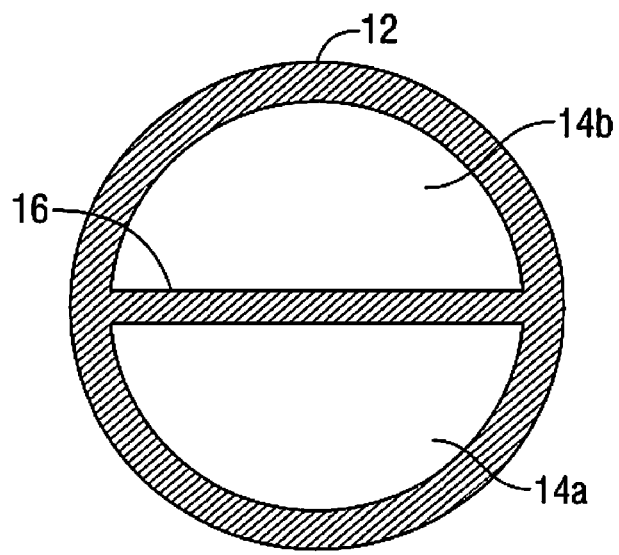
FIG. 2 is a cross-sectional view taken along section lines 2-2 of FIG. 1.

FIGS. 1 and 2 illustrate a multilumen catheter 10 which is formed using the method of manufacture discussed below. Catheter 10 includes an elongated catheter body 12 which defines a first lumen 14a and a second lumen 14b which are separated by a septum 16. Catheter body 12 includes a proximal end (not shown) and a distal end 12a. A separated tip section 20 is supported on the distal end 12a of catheter body 12 and includes a first tip member 20a and a second tip member 20b. As used herein, the term separated tip section means that the distal end of the catheter includes first and second tip sections which are disconnected along the longitudinal axis of the catheter such that the tip members can move or be moved in relation to each other. The first tip member 20a defines a longitudinal axes 24 and the second tip member 20b defines a second longitudinal axis 26. Longitudinal axis 24 and 26 define an angle β greater than 0 degrees. In one embodiment, β is greater than or equal to about 5 degrees and in another embodiment β is greater than or equal to about 10 degrees. In the illustrated embodiment, longitudinal axis 24 is substantially aligned with a longitudinal axis defined by catheter body 12. However, it is envisioned that both the first and the second longitudinal axes 24 and 26 may be angularly displaced from the longitudinal axis of catheter body 12. See, for example, FIG. 5.

Each tip member 20a and 20b defines a tip lumen 28 and 30, respectively, which has an open distal end 28a and 30a, respectively. Lumen 28 of tip member 20a is in fluid communication with lumen 14a (FIG. 2) of catheter body 12 and lumen 30 of tip member 20b is in fluid communication with lumen 14h of catheter body 12. In the embodiment illustrated in FIG. 1, tip member 20b has a longitudinal length which is greater than the longitudinal length of tip member 20a. In one embodiment, tip member 20b has a length which exceeds the length of tip member 20a by between about 5 mm or more. Alternatively, the lengths of tip members 20a and 20b may be substantially the same.

Figure 3:
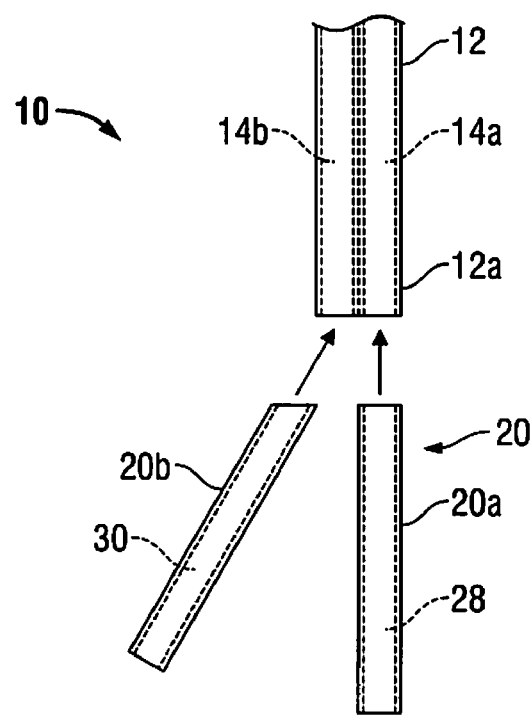
FIG. 3 is a top view of the multilumen catheter shown in FIG. 1 during a first embodiment of the presently disclosed method of manufacturing with the tip sections of the multilumen catheter separated from the catheter body.

FIG. 3 illustrates catheter 10 during the presently disclosed manufacturing process. As discussed above, catheter 10 includes a catheter body 12 having a distal end 12a, and a separated tip section 20 having a first tip member 20a and a second tip member 20b. Catheter body 12 defines first and second lumens 14a and 14b and first and second tip members 20a and 20b define tip lumens 28 and 30. During the method of manufacturing catheter 10, dual lumen catheter body 12, first tip member 20a and second tip member 20b are formed independently. This can be accomplished using any known manufacturing technique including, as discussed above extrusion and/or injection molding. In one embodiment, each of dual lumen catheter body 12, first tip member 20a and second tip member 20b is formed using an extrusion process. After each of the components are extruded, the first tip member 20a is assembled, i.e., secured or fastened, to distal end 12a of the dual lumen catheter body 12 such that tip lumen 28 of tip member 20a is fluidly coupled to first lumen 14a of catheter body 12. Next, the second tip member 20b is assembled to distal end 12a of dual lumen catheter body 12 such that tip lumen 30 is fluidly coupled to second lumen 14b of catheter body 12. First and second tip members 20a and 20b can be assembled to dual lumen catheter body 12 using heat, such as by welding, to effect covalent bonding of the thermoplastic resins of catheter body 12 and the first and second tip members 20a and 20b. Alternatively, first and second tip members 20a and 20b can be assembled to catheter body 12 using an adhesive, e.g., a slurry formulated from at least one solvent and at least one material capable of bonding to both the tip members 20a and 20b and the catheter body 12. Yet in another embodiment, the tip members 20a and 20b can be ultrasonically welded to one another, wherein ultrasonic energy is utilized to heat the contact areas of the components and form a bond. It is noted, that the tip members 20a and 20b, as well as the catheter body 12, can be cut or formed in any geometry to increase the surface area where these components contact one another. This is noted as it has been found that the greater the surface area the greater the bond strength will be.

Figure 4:
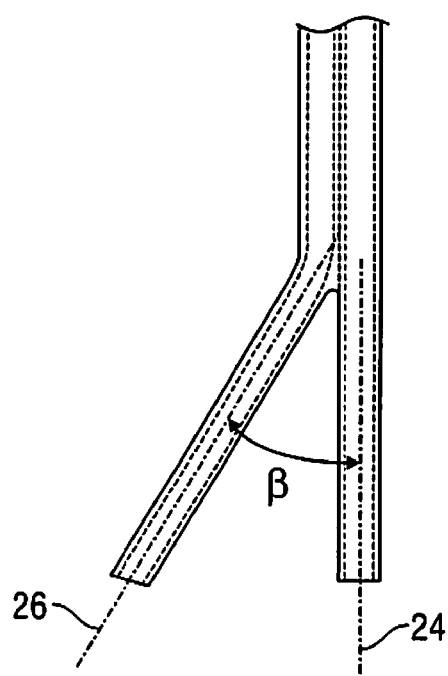
FIG. 4 is a top view of the multilumen catheter shown in FIG. 3 assembled.

As illustrated in FIG. 4, in one embodiment, first tip member 20a is assembled to catheter body 12 such that the longitudinal axis 24 of tip member 20a is substantially parallel to the longitudinal axis 25 of catheter body 12 and second tip member 20a is assembled to catheter body 12 such that the longitudinal axis 26 of tip member 20b is positioned to define an angle β, which is greater than 0 degrees, with respect to the longitudinal axis 24 of tip member 20a. In one embodiment, angle β is about 5 degrees or greater. In another embodiment, angle β is about 10 degrees or greater.

Figure 5:
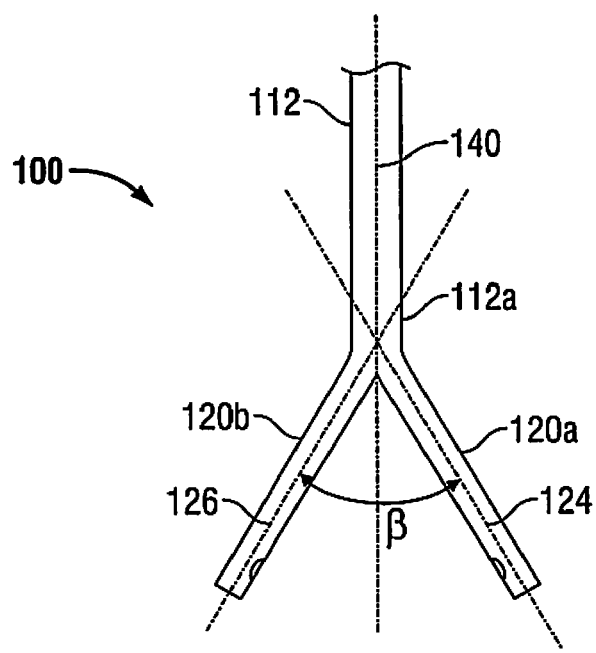
FIG. 5 is a top view of an alternative embodiment of the multilumen catheter formed using the manufacturing method disclosed herein.

In an alternative embodiment of the presently disclosed method shown in FIG. 5, each of tip members 120a and 120b of catheter 100 is assembled to distal end 112a of catheter body 112 such that the longitudinal axes 124 and 126 of tip members 120a and 120b are disposed at an angle to the longitudinal axis 140 of catheter body 112 and define an angle β therebetween. As discussed above, in one embodiment, angle β is about 5 degrees or greater and in a second embodiment angle β is about 10 degrees or greater. In one embodiment, tip members 120a and 120b are symmetrically positioned about the longitudinal axis of the catheter body 112. In this embodiment, either lumen 120a or 120b of catheter 100 may function as the arterial lumen or the venous lumen during a hemodialysis procedure.

Figure 6:
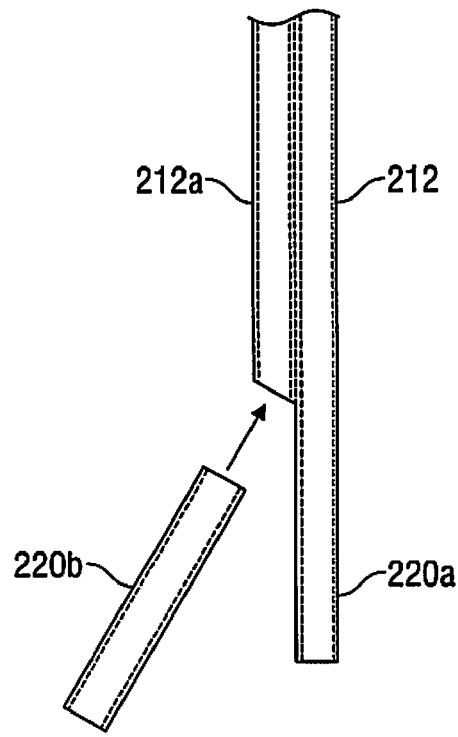
FIG. 6 is a top view of the multi-lumen catheter shown in FIG. 1 during a second embodiment of the presently disclosed method of manufacturing with one tip section separated from the catheter body.

Referring to FIG. 6, in an alternative embodiment of the presently disclosed manufacturing method, dual lumen catheter body 212 of catheter 200 is formed to include tip member 220a and tip member 220b is formed separately. As discussed above, catheter body 212 and tip member 220b can be formed using a variety of manufacturing techniques including an extrusion process. Next, tip member 220b is assembled to distal end 212a of catheter body 212, using heating or adhesives, such that the longitudinal axis 226 of tip member 220b is disposed at angle β with respect to the longitudinal axis 224 of tip member 222a. As discussed above, angle β is greater than 0 degrees, and can be about 5 degrees or greater or, alternatively, about 10 degrees or greater. In one exemplary manufacturing process, catheter body 212 is extruded. Therefrom, a portion of the catheter is removed, using a cutting process (e.g., skiving using a blade, laser cutting, etc.), to form tip member 220b. Tip member 220a is formed using a separate extrusion process and then thermally bonded to catheter body 212. The thermal bonding process is achieved by inserting mandrels, which are herein defined as longitudinal members capable of fitting within both the catheter body 212 and the tip members 220a and 220b and can withstand the thermal energy encountered during the thermal bonding process without significant deformation. With a first mandrel inserted into distal end 212a and extending into tip member 220b and a second mandrel extending from catheter body 212 into tip member 220a, thermal energy can be applied to the assembly to effectively bond the components together. The thermal energy can be applied either by using a die or by using shrink tubing. If shrink tubing is used, a first shrink tube can be inserted over the tip member 220a and thermal energy can be applied thereto (e.g., using a heat gun) to shrink the shrink tube thereon. A second shrink tube can then be assembled over the first shrink tube, having tip member 220a and its mandrel therein, and also over tip member 220b and it's mandrel (i.e., effectively having both tip members 220a and 220b and both mandrels therein. This second shrink tube can then extend up at least a portion of the catheter body 212. Thermal energy can then be applied to the second shrink tube to join tip member 220b to distal end 212a. It is noted that the shrink tubing will be chosen such that it does not bond to the material employed for the catheter, such as olefins.

As illustrated in FIGS. 3 and 6, the distal end surface 250 of catheter body 212 (FIG. 6) and/or the proximal end of tip member 50 (FIG. 3) may be angled or tapered such that the distal surface of catheter body 12, 212 and the proximal surface of tip member 20b, 220b abut to define the desired angle β. Catheter body 12, 212 and/or tip member 20b, 220b can be angled during the forming process, or alternatively, during a subsequent machining process, e.g., cutting, grinding, shaving, thermal tip forming, etc.

Referring again to FIG. 5, one or more sideholes 142 can be formed on either or both of tip members 120a and 120b to provide additional fluid flow paths for fluid to flow into or from catheter 100. Sideholes 142 can be dispersed in any configuration or orientation about one or both tip members 120a and 120b. In one embodiment shown in FIG. 5, a sidehole 142 is positioned on the tip members 120a and 120b at a location to reduce the chance of positional occlusion. More specifically, a sidehole 142 is positioned on each of tip members 120a and 120b to face the adjacent tip member to minimize any likelihood of occlusion by adjacent walls of tissue, e.g., veins, heart tissue, etc., within a patient. Although sideholes 142 are only illustrated with respect to catheter 100, sideholes may also be included on catheters 10 and 200.

Although specific features of the disclosure are shown in some drawings and not in others, this is for convenience only as each feature may be combined with any or all of the other features in accordance with the disclosure.

It will be understood that various modifications may be made to the embodiments disclosed herein. For example, the various manufacturing processes disclosed to manufacture dual lumen catheters with expandable lumens may also be used to form a single lumen catheter with an expandable lumen where applicable. Therefore, the above description should not be construed as limiting, but merely as exemplifications of embodiments. Those skilled in the art will envision other modifications within the scope and spirit of the claims appended hereto.

What is claimed is:

1. A method of manufacturing a multilumen catheter having a separated tip configuration, the method comprising the steps of:
   assembling a second distal tip member to a distal end of a catheter body such that the second distal tip member is in fluid communication with a second lumen of the catheter body, the catheter body defining a first longitudinal axis and including a first distal tip member at the distal end of the catheter body, the first distal tip in fluid communication with a first lumen of the catheter body, the step of assembling including:
   positioning a first shrink tube over the second distal tip member and applying thermal energy to the first shrink tube; and
   positioning a second shrink tube over the first shrink tube and over the first distal tip member and applying thermal energy to the second shrink tube.

2. The method according to claim 1, wherein the first distal tip member defines a first distal lumen portion, the second distal tip member defines a second distal lumen portion, and assembling includes positioning a first mandrel in the distal end of the first lumen of the catheter body and the first distal lumen portion and positioning a second mandrel into the distal end of the second lumen of the catheter body and the second distal lumen portion prior to applying thermal energy to the first and second shrink tubes.

3. The method according to claim 1, further including the step of positioning the second distal tip member along a second longitudinal axis, the second longitudinal axis at an angle β in relation to the first longitudinal axis of the catheter body.

4. The method according to claim 3, wherein the step of positioning the second distal tip member includes setting the angle β at 5 degrees or greater.

5. The method according to claim 3, wherein the step of positioning the second distal tip member includes setting the angle β at 10 degrees or greater.

6. The method according to claim 1, further comprising removing a distal portion of the catheter body to define the first distal tip member at the distal end of the catheter body.

7. The method according to claim 1, further comprising assembling the first distal tip member to the distal end of the catheter body along a third longitudinal axis.

8. The method according to claim 7, wherein assembling the second distal tip member to the distal end of the catheter body includes positioning the second distal tip member along a second longitudinal axis and securing the first and second distal tip members to the catheter body such that the second longitudinal axis is disposed at an angle β to the third longitudinal axis, and the angle β is greater than 0 degrees.

9. The method according to claim 7, wherein the first and second distal tip members are symmetrical about the first longitudinal axis.

10. The method according to claim 1, further comprising forming sideholes in at least one of the first and second distal tip members.

11. A method of manufacturing a multilumen catheter having a separated tip configuration, the method comprising the following steps:
   i) extruding a catheter body having a proximal end and a distal end and defining a first lumen and a second lumen, the catheter body defining a first longitudinal axis;
   ii) removing a distal portion of the catheter body to define a first distal tip member at the distal end of the catheter body, the first distal tip member defining a first distal lumen portion in fluid communication with the first lumen of the catheter body;

iii) extruding a second distal tip member defining a second distal lumen portion; and iv) thermally bonding the second distal tip member to the distal end of the catheter body such that the second distal lumen portion communicates with the second lumen of the catheter body, the step of thermally bonding including:

positioning a first shrink tube over the second distal tip member and applying thermal energy to the first shrink tube; and positioning a second shrink tube over the first shrink tube and over the first distal tip member and applying thermal energy to the second shrink tube.

12. The method according to claim 11, wherein the step of thermally bonding includes positioning a first mandrel in the distal end of the first lumen of the catheter body and the first distal lumen portion and positioning a second mandrel into the distal end of the second lumen of the catheter body and the second distal lumen portion prior to applying thermal energy to the first and second shrink tubes.

13. The method according to claim 11, further comprising positioning the second distal tip member along a second longitudinal axis, the second longitudinal axis at an angle β in relation to the first longitudinal axis of the catheter body.

14. The method according to claim 13, wherein positioning the second distal tip member includes setting the angle β at 5 degrees or greater.

15. The method according to claim 13, wherein positioning the second distal tip member includes setting the angle β at 10 degrees or greater.

16. The method according to claim 13, further comprising cutting at least one of the distal end of the catheter body and a proximal end of the second tip member at an angle such that a distal end surface of the catheter body and a proximal end surface of the second tip member abut to define the angle β.

17. The method according to claim 11, further comprising forming sideholes in at least one of the first and second distal tip members.

* * * * *